(12) United States Patent
Anderson

(10) Patent No.: US 6,491,929 B1
(45) Date of Patent: Dec. 10, 2002

(54) SKIN COSMETICS

(75) Inventor: Richard R. Anderson, Lexington, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/516,685

(22) Filed: Mar. 1, 2000

Related U.S. Application Data (60) Provisional application No. 60/122,457, filed on Mar. 1, 1999.

(51) Int. Cl.[7] .............................. A61K 7/00; A61K 9/14; A61K 9/16
(52) U.S. Cl. .................... 424/401; 424/489; 424/490
(58) Field of Search ........................ 424/401, 489, 424/490

(56) References Cited

U.S. PATENT DOCUMENTS

| | | | |
|---|---|---|---|
| 4,756,906 A | 7/1988 | Sweeny ..................... 424/63 |
| 4,929,693 A | 5/1990 | Akashi et al. ............ 526/259 |
| 5,166,345 A | 11/1992 | Akashi et al. ............. 544/71 |
| 5,176,905 A | 1/1993 | Ohno et al. ................ 424/69 |
| 5,198,470 A * | 3/1993 | Zysman et al. ............ 514/785 |
| 5,223,559 A * | 6/1993 | Arraudeau et al. .......... 524/47 |
| 5,229,104 A | 7/1993 | Sottery et al. ............ 424/59 |
| 5,294,444 A * | 3/1994 | Nakaura et al. ............ 424/401 |
| 5,486,354 A | 1/1996 | Defossez et al. ........... 424/63 |
| 5,508,034 A | 4/1996 | Bernstein ................. 424/401 |
| 5,626,839 A | 5/1997 | Scales-Medeiros ......... 424/59 |
| 5,628,934 A | 5/1997 | Ohno et al. ............... 252/586 |
| 5,631,012 A | 5/1997 | Shanni .................... 424/401 |
| 5,688,831 A | 11/1997 | El-Nokaly et al. ......... 514/938 |
| 5,695,745 A | 12/1997 | Barton et al. ............. 424/49 |
| 5,730,960 A | 3/1998 | Stein et al. .............. 424/59 |
| 5,730,972 A * | 3/1998 | Simon et al. .............. 424/59 |
| 5,733,895 A | 3/1998 | Forestier et al. .......... 514/63 |
| 5,744,125 A | 4/1998 | Pawelek et al. ............ 424/59 |
| 5,753,244 A | 5/1998 | Reynolds et al. .......... 424/401 |
| 5,762,913 A | 6/1998 | Tanaka et al. ............. 424/59 |
| 5,762,915 A | 6/1998 | Saito et al. .............. 424/59 |
| 5,776,470 A | 7/1998 | Schmidt .................. 424/401 |
| 5,776,480 A | 7/1998 | Candau et al. ............ 424/401 |
| 5,798,091 A | 8/1998 | Trevino et al. ........... 424/401 |
| 5,874,091 A * | 2/1999 | Grollier ................. 424/401 |

OTHER PUBLICATIONS

R. Rox Anderson, MD "Polarized Light Examination and Photography of the Skin"—Anderson Arch Dermatol Jul. 1991, vol. 127.

* cited by examiner

Primary Examiner—Thurman K. Page
Assistant Examiner—S. Tran
(74) Attorney, Agent, or Firm—Fish & Richardson P.C.

(57) ABSTRACT

An anti-reflective cosmetic composition for skin is disclosed. The composition includes a material that, when applied to skin, forms a layer of the material that adheres to the skin, has a thickness of from about 60 nm to about 140 nm, and a refractive index of between about 1.1 and 1.4. The layer reduces the Fresnel component of light reflected from skin. In addition, cosmetic compositions that include colored, shaped additives that mimic the appearance of colored structures in healthy skin are disclosed.

38 Claims, 3 Drawing Sheets

SKIN COSMETICS

CROSS-REFERENCE TO RELATED APPLICATION

This application claims priority from a provisional application, U.S. application Ser. No. 60/122,457, filed on Mar. 1, 1999.

FIELD OF THE INVENTION

The invention relates to skin cosmetics.

BACKGROUND OF THE INVENTION

Skin cosmetics are generally designed to give skin a more youthful, healthy appearance. One aspect of this goal is reducing the visibility of wrinkles and eliminating oily glare. Most existing skin cosmetics are creams or powders which, when applied to skin, create an opaque layer which hides wrinkles and diffuses reflected light. Covering skin with an opaque substance, however, can give skin a homogenous, unnatural appearance.

SUMMARY OF THE INVENTION

The invention is based on the discovery that if a cosmetic layer or coating is applied to skin that specifically reduces the Fresnel component of reflectance, without affecting other skin optics parameters, the coating will obscure wrinkles and give the skin a more natural, youthful appearance. In addition, by including in a skin cosmetic colored additives that mimic natural chromophoric structures in skin, the overall appearance of the cosmetic will be more lifelike and natural.

In general, in one aspect, the invention features an anti-reflective cosmetic composition for skin. The composition includes a material that, when applied to skin, forms a layer of the material that adheres to the skin, has a thickness of from about 60 nm to about 140 nm and a refractive index of between about 1.1 and 1.4. The layer reduces the Fresnel component of light reflected from skin.

Embodiments of this aspect of the invention can include one or more of the following features. The layer has a thickness of between about 80 nm and 120 nm, e.g., 95–100 nm, and a refractive index of between about 1.2 and 1.3, e.g., 1.22. The layer can be a molecular monolayer including amphipathic molecules, such as straight-chain phospholipids. The amphipathic molecules can have lengths of between about 95 nm and 100 nm. In addition, the layer can include a trapped gas to reduce the index of refraction of the layer. The trapped gas can be in one or more microspheres or microbubbles having diameters less than about 55 nm. The composition can also include a carrier, such as water.

Alternatively, the molecular monolayer can include a monomer, where the monomer, when activated, polymerizes to form the molecular monolayer. The monomer includes a negatively charged moiety, such as an amine group or a carboxyl group, that is attracted to stratum corneum. Activation of the monomer can be triggered by application of the material to skin. The cosmetic composition can also be an aerosolizable liquid that can be sprayed onto skin to form the layer.

The cosmetic composition can further include a chromophore having a natural skin color. The chromophore can be, e.g., melanin granules or liganded hemoproteins. The layer formed by the composition can be generally translucent or transparent.

Instead of a molecular monolayer, the layer can be, e.g., a monolayer including a trapped gas to reduce the refractive index. The trapped gas can be in one or more microspheres or microbubbles. The layer can include microspheres and can further include a packing agent. The packing agent is, e.g., a polymer such as polyvinylalcohol, polymethyl methacrylate, polydimethyldiallylammonium. The microspheres can be encapsulated by a capsule substance having a negatively charged moiety, such as a polycarbonate group.

In another aspect, the invention features a method of reducing Fresnel reflectance from skin. The method includes applying a cosmetic composition to skin, such that a material in the composition forms a layer on the skin. The layer has a thickness of between about 60 nm and 140 nm and a refractive index of between about 1.1 and 1.4.

Embodiments of this aspect of the invention can include one or more of the following features. The layer is a monolayer. The composition includes a carrier, and the method further includes removing carrier and non-bound material from the skin, e.g., by washing or allowing the carrier to evaporate after formation of the monolayer, such that only the monolayer remains on the skin.

In another aspect, the invention features a cosmetic composition having colored, shaped additives that mimic the appearance of colored structures in healthy skin and a carrier. The additives are mixed into the carrier in an amount sufficient to mimic spectral texture of healthy skin when applied to the skin.

Embodiments of this aspect of the invention can include one or more of the following features. The carrier can include a chromophore having a natural skin color, e.g., the color of melanin or oxyhemoglobin. The colored structures mimicked by the additives can be mimics of natural structures in skin such as hair follicles, sweat duct openings, fine hairs, freckles, or blood vessels. The additives can be dyed polymers, and have shapes such as threads, disks, or beads. The composition can further include a material that forms a layer when the material is applied to skin. The layer has a thickness of between about 60 nm and 140 nm and a refractive index of between about 1.1 and 1.4.

An "amphipathic molecule" is a molecule having a polar end and a lipophilic end.

As used herein, "spectral texture" describes the spatial variation in the reflectance spectrum caused by endogenous skin pigments localized in structures such as blood vessels, freckles, vellus hairs, pores, and follicles.

As used herein, a microsphere is a small sphere of a capsule substance, e.g., albumin or a natural or synthetic polymer, that surrounds a gas. A microbubble is a small pocket of gas within a solid or liquid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

The new cosmetics provide the advantage of reducing the visibility of wrinkles and coarse details in skin without affecting other skin optics parameters, such as spectral texture and color, to give the skin a more natural, youthful appearance. The anti-reflective cosmetics are non-toxic and are easy to apply. In addition, the new cosmetics that include colored additives allow wrinkles and skin blemishes to be obscured, without making the skin appear homogenous and unnatural. Sunscreens and moisturizers can easily be added to the new cosmetic compositions.

Other features and advantages of the invention will be apparent from the following detailed description, and from the claims.

DETAILED DESCRIPTION

Embodiments of the invention include skin cosmetics which, when applied to skin, create a translucent or transparent anti-reflective layer or coating. Light waves reflected from the coating interfere with waves reflected from the surface of the skin, thereby reducing the Fresnel component of reflectance and obscuring the visibility of wrinkles and fine details in the skin, without affecting other skin optics parameters, such as spectral texture and color.

The invention also includes addition of colored additives to cosmetics. The colored additives mimic natural chromophoric structures, giving the cosmetic a more natural and lifelike appearance when applied to skin.

Anti-Reflective Cosmetic Layers And Coatings

Incident light waves that reach the surface of skin either reflect off the surface or penetrate into the skin's tissue. The image of skin we see is a combination of two components: the light reflected at the surface, called the "Fresnel" or "regular" component, and light back-scattered by internal structures within the tissue. The Fresnel component of reflectance follows Fresnel's reflection equations and accounts for the "glare" or "shine" from skin. The Fresnel component also provides details of surface structure. See, generally R. Rox Anderson, "Polarized Light Examination and Photography of the Skin," *Archives of Dermatology*, 27:1000–1005 (1991).

When the Fresnel component of skin reflectance is reduced or eliminated, surface details become less visible. Fine wrinkles and surface markings disappear, and the skin appears soft and diffuse, but still focused. Thus, reduction of the Fresnel component of skin reflectance eliminates many of the traditional visual cues of skin aging.

Fresnel reflection from the skin's surface can be reduced by applying an anti-reflective cosmetic layer or coating. In general, the new anti-reflective cosmetic coatings have a thickness of about ¼ of the wavelength of ambient light, and an index of refraction about equal to the square root of the index of refraction of the stratum corneum, the outermost layer of skin. When a coating having these characteristics is applied to the skin, light which strikes the coated surface is reflected with a reduced Fresnel component, since light waves reflected from the surface of the coating will be off-phase by about ½ wavelength from light waves reflected from the surface of the skin, and the waves will destructively interfere.

The condition that the index of refraction of the layer or coating, nM, be approximately equal to the square root of the index of refraction of skin, $n_s$, is derived from Fresnel's equation, where reflectance, R, at normal incidence is given by:

$$R=[(1-n_c)/(1+n_c)]^2-[(n_c-n_s)/(n_c+n_s)]^2$$

where the first term is reflectance from the coating, and the second term is reflectance from skin. From the above equation, the reflectance equals zero when $n_c=n_s^{1/2}$.

The precise thickness of an effective anti-reflective cosmetic coating depends upon the angle of incidence of a light source, the indexes of refraction of the coating and the ambient medium, and the nature of the coating material (whether the material causes an abrupt phase change for incident light). When air is the ambient medium, the angle of incidence is 90° relative to the surface, and the coating material does not cause an abrupt phase change, then the thickness of the anti-reflective coating should be about $\lambda/4n_c$, where $\lambda$ is the wavelength of ambient light and $n_c$ is the index of refraction of the coating. If the material does cause an abrupt phase change, then the thickness can be varied to compensate. If the angle of incidence is less than 90°, then the thickness of the coating should be reduced to account for the longer light path through the coating.

In general, the closer an anti-reflective cosmetic coating's thickness and index of refraction are to the suggested parameters, the more thoroughly it will reduce Fresnel reflectance. However, a coating which has parameters close to, but not identical to, the suggested parameters will still reduce Fresnel reflectance to some extent.

The outermost layer of skin, the stratum corneum, has an index of refraction between about 1.45 and 1.55. The center of the visible light spectrum has a wavelength of about 550 nm. An anti-reflective cosmetic layer or coating for skin, therefore, for light having an incident angle of 90° and using a material which does not cause an abrupt phase change, should have an index of refraction of, e.g., $(1.5)^{1/2}=1.22$, and a thickness of, e.g., $\lambda/4(1.5)^{1/2}$, or about 105–115 nm. Assuming a light source having an incident angle of, e.g., about 30° (a better estimate for a light source illuminating a human face), then the length of the light path through the coating will be greater than the thickness of the coating by a factor of, e.g., about 1/cos 30°. Thus, for an incident angle of about 30°, the desired thickness should be reduced by multiplying by, e.g., about cos 30°, reducing the desired thickness, e.g., to about 90–100 nm, e.g., 95 nm.

In the sections below, two types of compositions capable of forming the desired anti-reflection coating are described: compositions that form molecular monolayers, and compositions that form trapped gas monolayers.

Compositions That Form Molecular Monolayers

A first type of cosmetic composition capable of forming a coating having the above parameters is a cream that includes a molecular monolayer-forming material and a carrier. In this composition, the molecular monolayer-forming material controls the thickness of the coating.

The monolayer-forming material can include, e.g., straight chain phospholipids having lengths of, e.g., about 95–100 nm, that form a molecular monolayer when applied to the surface of skin. The straight-chain phospholipids have non-polar ends that are attracted, e.g., by Van der Waals forces, to the lipophilic surface of the stratum corneum, and polar ends that will orient away from the skin. The polar ends can include, e.g., carboxyl, phosphate, or amine groups. Such straight-chain phospholipids can include, e.g., extended and saturated polyethylene glycols, or extended versions of straight-chain phospholipids that occur naturally. Other types of amphipathic molecules, including, e.g., nontoxic detergents, unsaturated phospholipids, and copolymers can also be used.

Alternatively, the layer-forming material that forms the molecular monolayer can be formed from a polymer. In this embodiment, the lotion would include a monomer that polymerizes when exposed to the stratum corneum, or when exposed to a polymerizing agent applied along with or after application of the lotion. The monomer should have a moiety which is attracted to the stratum corneum, e.g., by Van der Waals forces, covalent bonding, or ionic bonding, such that after polymerization, the stratum corneum will be coated by a layer of the polymer. The attracted moiety can be, for example, an amine group or a carboxyl group. Polymerization can be triggered using, e.g., activators such as heat, ultraviolet radiation, or an agent that generates free radicals. Alternatively, a monomer that polymerizes when exposed to air, such as silicone rubber, could be used, obviating the need for an activator. The thickness of the layer can be controlled, e.g., by limiting the quantity of the monomer or the activator, by controlling the ratio of the monomer to the activator, by limiting the amount of time the monomer is exposed to an activator, or by using pre-formed particles having desired effective sizes.

The carrier can be water, or some other polar compound that evaporates readily, such as an alcohol. Oils can also be used. Additional ingredients can be included in the composition, such as preservatives, a sunscreen, a moisturizer, or materials that alter the viscosity of the lotion.

Figure 1A:
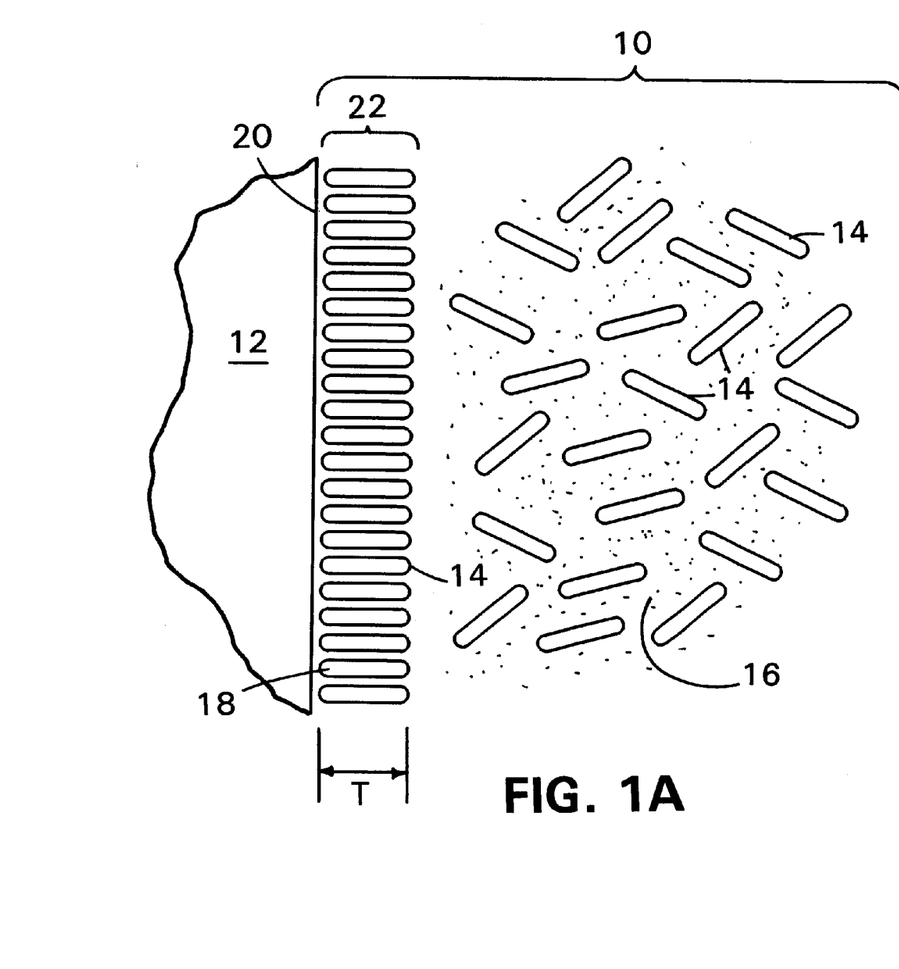
FIGS. 1A and 1B are enlarged views of a cosmetic layer or coating applied to the surface of skin.
Figure 1B:
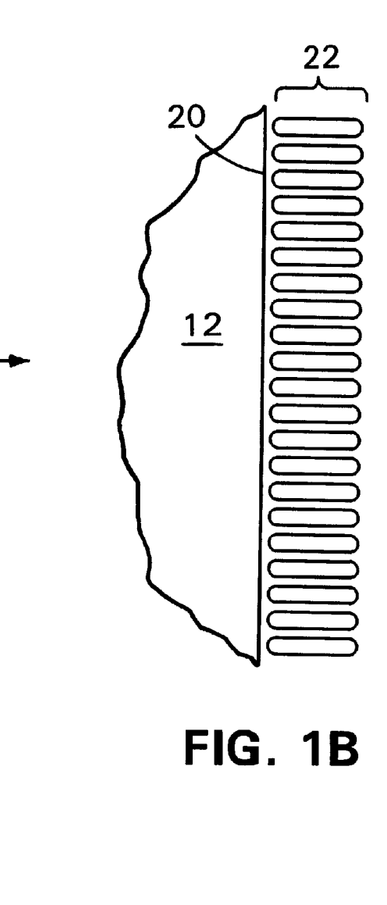

FIGS. 1A and 1B illustrate how a lotion including amphipathic molecules forms a molecular monolayer on the user's skin. Referring to FIG. 1A, an individual first applies a lotion 10 to skin 12. Lotion 10 includes amphipathic molecules 14 and a water carrier 16. Non-polar ends 18 of some amphipathic molecules 14 orient toward the surface 20 of skin 12, coating surface 20 with a molecular monolayer 22 having a thickness $T_1$, where $T_1$ is, e.g., about 95–100 nm. Next, the user washes skin 12, e.g., with water, to remove excess carrier 16 and amphipathic molecules 14 not bound to surface 20, leaving only molecular 30 monolayer 22, as shown in FIG. 1B. Alternatively, instead of washing skin 12, the user can wait for carrier 16 to evaporate, and then brush off excess residue left by the amphipathic molecules 14 which are not part of molecular monolayer 22.

After washing, the user can also add a cross-linking agent to cross-link the amphipathic molecules in monolayer 22. Cross-linking the molecules would solidify monolayer 22, allowing the anti-reflective coating to remain on skin 12 for a longer period of time. Cross-linking agents can include, e.g., aldehydes, such as glutaraldehyde, formaldehyde, ketosugars, such as dihydroxyacetone, and homogentisic acid.

For a molecular monolayer to be an anti-reflective coating, the index of refraction of the layer should be between about 1.2 and 1.3. A molecular monolayer consisting primarily of phospholipids will likely have an index of refraction greater than the desired index. Thus, if phospholipids (or some other material having an index of refraction greater than the desired level) are used, the index of refraction of the layer should be reduced by including an additional substance in the layer.

Figure 2:
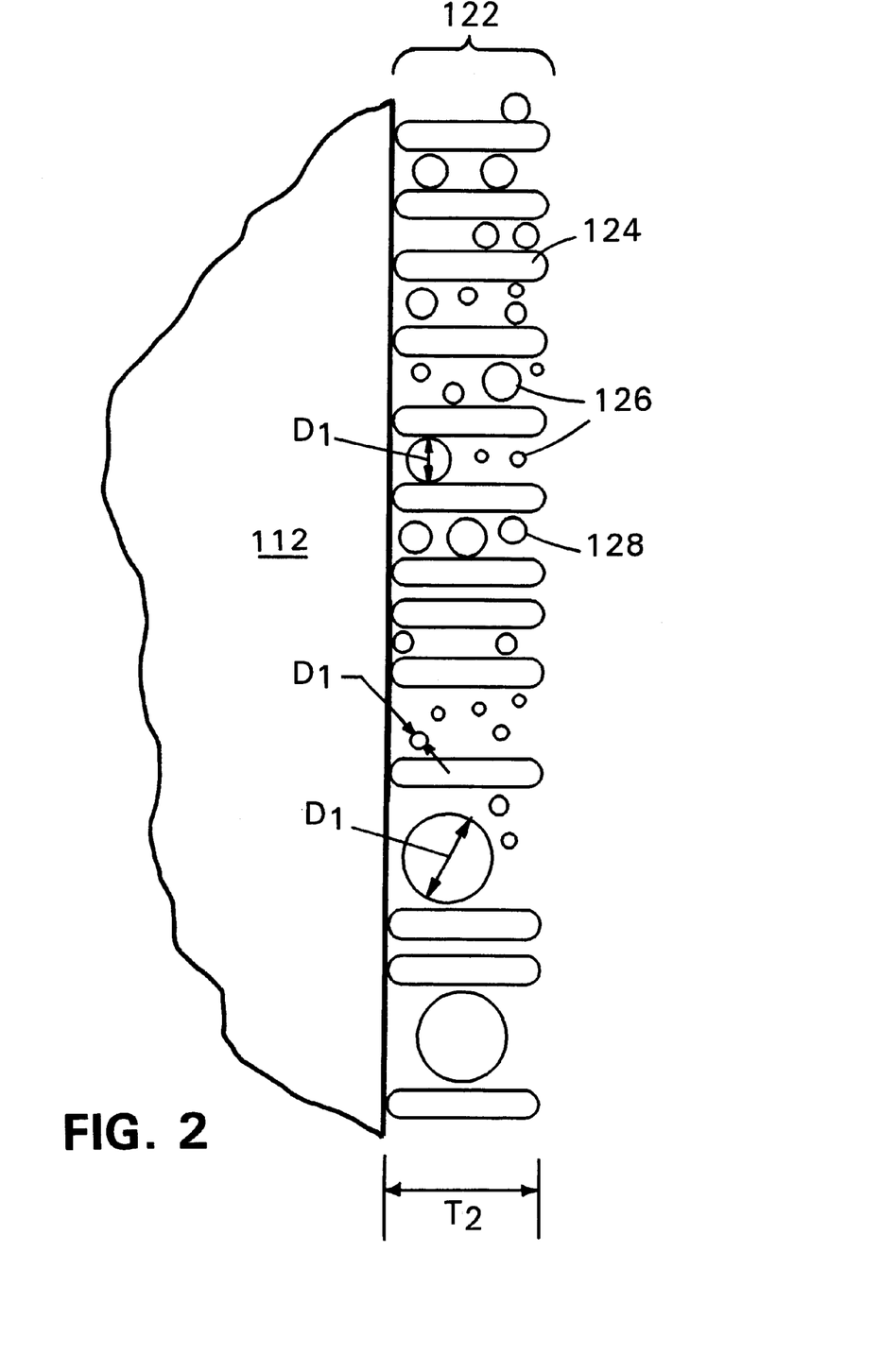
FIG. 2 is an enlarged view of a cosmetic layer or coating of including microbubbles applied to the surface of skin.

For example, the index can be lowered to the desired level by trapping a gas, e.g., air, in the layer by including stable microbubbles in the layer. Referring to FIG. 2, a molecular monolayer 122 coating skin 112 includes amphipathic molecules 124 and microbubbles 126. Monolayer 122 has a thickness $T_2$ of about 95–100 nm. Air pockets 128 in microbubbles 126 will have an index of refraction of about 1.0. Thus, a layer including both microbubbles 126 and amphipathic molecules 124 will have a composite index of refraction between 1.0 and the index of refraction of amphipathic molecules 124. The number and size of microbubbles 126 can be varied so that the composite index of refraction is between about 1.2 and 1.3. Microbubbles 126 can have various diameters $D_1$ smaller than, e.g., about 55 nm, to minimize Rayleigh scattering. Alternatively, diameters $D_1$ can be greater than 55 nm.

Microbubbles 126 can be added to molecular monolayer 122 by adding microbubbles to the lotion initially applied by the user. Microbubbles can be added to the lotion by, e.g., injecting air or other gas into the lotion during production or by "whipping-up" the lotion in a manner that generates bubbles.

Instead of whipping microbubbles into the lotion, microspheres having the desired diameters $D_1$ can be produced separately and added to the lotion. In general, the diameters and stability of pre-formed microspheres can be more easily controlled than the diameters and stability of "whipped-up" microbubbles. Techniques for producing microspheres from, e.g., albumin, are known. Useful microspheres include those used as ultrasound contrast agents, which can be purchased commercially from, e.g., NYCOMED, SA, in Sweden.

The diameters of the microbubbles or microspheres may depend on the temperature of their surroundings. For example, the microbubbles or microspheres might expand when the lotion is applied to the user's skin. In some applications, therefore, the diameters of the microbubbles or microspheres added to the lotion may be smaller than the desired diameters $D_1$ of microbubbles 126.

The index of refraction of the monolayer can also be lowered by including porous glass fragments, nanosponges, or nanocapsules containing a gas in the cosmetic, or by adding solutes having an index of refraction less than the desired level, e.g., less than 1.2–1.3. In addition, if necessary, the index of refraction of the layer can be increased by adding solutes having an index of refraction greater than the desired level.

The desired index of refraction, therefore, can be achieved by creating a layer having the layer forming material alone, the layer forming material with microbubbles or microspheres, or the layer forming material with both microbubbles or microspheres and various solutes.

Other variations of the molecular monolayer forming composition are possible. For example, rather than a lotion (solution) or a cream (oil-in-water suspensions), the cosmetic composition of the first embodiment can also be a liquid having a low viscosity, so that it can be aerosolized and sprayed onto skin. The thickness of the layer formed by the spray could be controlled by limiting the amount of spray applied, or by washing off excess material after formation of a monolayer, as described above. If the molecular monolayer includes a polymer rather than amphipathic molecules, the polymerizing agent could be sprayed onto the skin in addition to, or instead of, the monomer.

The cosmetic composition can be clear (largely transparent), or color can be added. For example, chromophores which mimic natural skin color, such as melanin granules or liganded hemoproteins (e.g., hemoglobins or cytochromes), can be added to the composition to add color. So long as the coating remains translucent, the addition of color will not significantly diminish the anti-reflective properties of the coating.

Trapped Gas Monolayer

Figure 3:
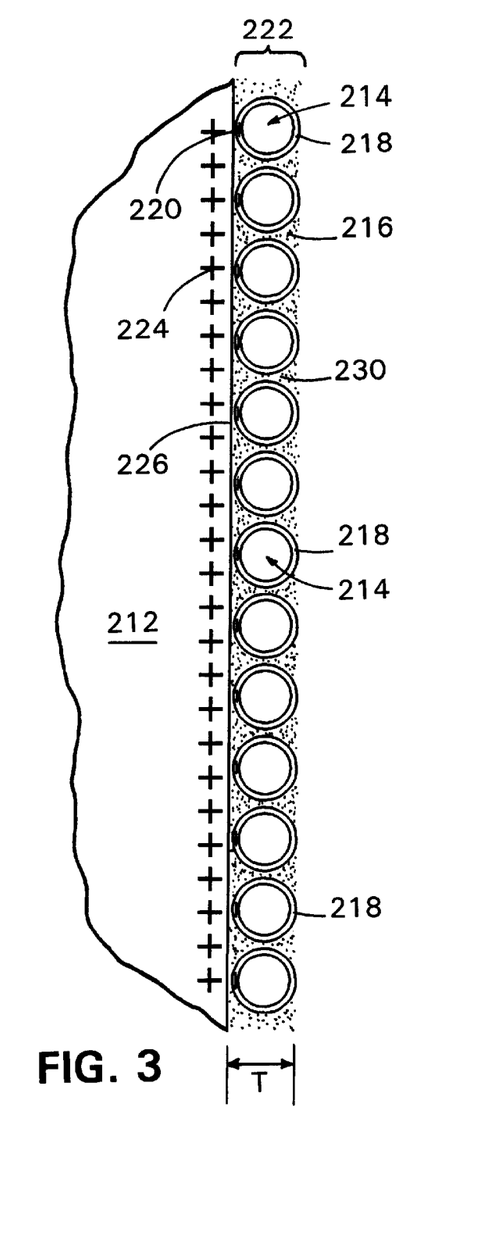
FIGS. 3 and 4 are enlarged views of alternative cosmetic coatings applied to the surface of skin.

The anti-reflective coating can also be formed as a monolayer containing trapped gas, e.g., air, within microspheres or microbubbles. Referring to FIG. 3, a monolayer 222 coating skin 212 includes microspheres 214 and packing agent 216. Microspheres 214 are capsules 218 having a negative charge 220 that enclose a volume of air or other gas having a refractive index of or near 1.0. Negative charge 220 attracts capsules 218 to positive charges 224 on the surface 226 of skin 212. Capsules 218 might include, e.g., a polycarbonate group having a negative charge. Microspheres 214 have various diameters $D_2$ averaging about 95–100 nm, and monolayer 222 has a thickness $T_3$ of, e.g., about 95–100 nm, which is controlled by diameters $D_2$ of microspheres 214.

Packing agent 216 can be, e.g., a polymer such as polyvinyl alcohol (PVA), polymethyl methacrylate (PMMA), or polydimethyldiallylammonium (PDDA). Packing agent 216 acts to fill spaces 230 between microspheres 214, and to help adhere microspheres 214 to skin 212, thereby solidifying monolayer 222.

The index of refraction of monolayer 222 will be a composite of the index of refraction $n_p$ of the packing agent 216, the index of refraction $n_{cap}$ of the capsules 218, and the index of refraction of the gas (near 1.0). In general, the index of refraction of monolayer 222, $n_1$, equals:

$$n_1 = (V_g) + n_p(V_p) + n_{cap}(V_{cap})$$

where $V_g$ is the fractional volume of monolayer 222 filled by trapped gas, $V_p$ is the fractional volume of monolayer 222 filled by the packing agent, and $V_{cap}$ is the fractional volume of monolayer 222 filled by capsule material (if present). The above fractional volumes can be adjusted to achieve the desired composite index of refraction of, e.g., about 1.2–1.3.

The microspheres or microbubbles will not cause significant scattering of the incident light, since non-absorbing particles less than 0.2 micrometers in thin layers, in general, are transparent. Here, the microspheres have diameters less than 0.2 micrometers and are closely packed, so any particle scattering which would normally be caused by encapsulated gas is reduced.

Microsphere monolayer 222 can be formed by applying a lotion including a packing agent 216 and microspheres 214, allowing microspheres 214 contacting skin 212 to automatically form a monolayer, and then washing off the microspheres 214 and packing agent 216 which are not part of the monolayer 222.

Alternatively, monolayer 222 can be formed by applying microspheres 214 and packing agent 216 separately. First, microspheres 214 can be introduced into a carrier, such as water, an alcohol, or an oil. Next, the carrier loaded with microspheres 214 is applied to skin 212. Microspheres 214 close to skin 212 will be attracted to skin, forming a monolayer. Excess carrier and non-bound microspheres 214 can be washed off or allowed to evaporate. Packing agent 216 can then be applied on top of microspheres 214. Packing agent 216 will fill spaces 230 between microspheres 214, and will pack microspheres 214 to skin 212, forming monolayer 222.

In addition, it is possible to form a monolayer without using a packing agent. In this embodiment, monolayer 222 would include only the encapsulated microspheres 214 bound to the stratum corneum. The microspheres would have diameters of, e.g., about 95–100 nm, and composite indexes of refraction of, e.g., about 1.2–1.3. The step of adding a packing agent would be eliminated.

Figure 4:
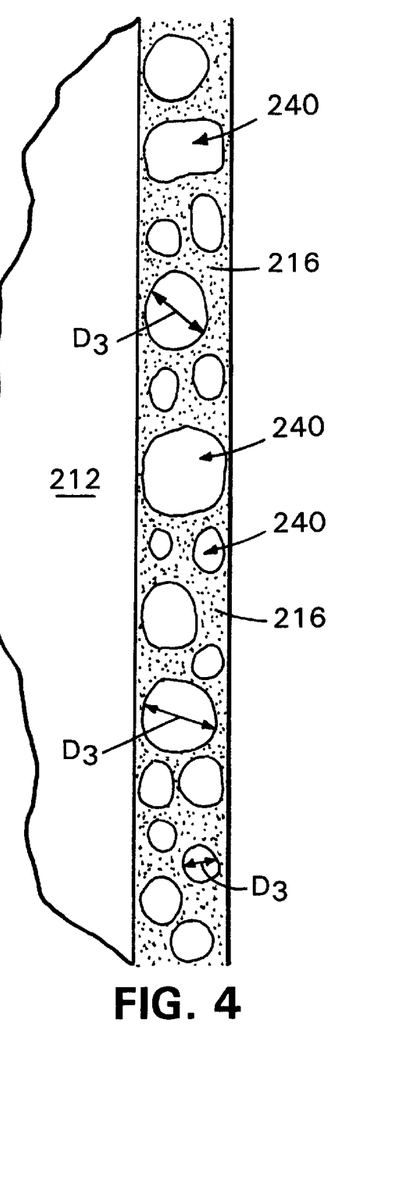

Referring to FIG. 4, instead of charged microspheres 214, trapped gas monolayer 222 can include microbubbles 240 having various diameters $D_3$ of, e.g., about 95–100 nm. The thickness of monolayer 222 in this embodiment is controlled by the diameters $D_3$ of microbubbles 240. In this embodiment, a lotion including microbubbles 240 and packing agent 216 can be made by "whipping-up" packing agent 216 during manufacture to produce bubbles, by injecting air or another gas, e.g., nitrogen, into packing agent 216 to form bubbles, or by inducing a phase change in packing agent 216 as it polymerizes. A phase change can be induced, for example, by varying the pressure or temperature of agent 216 during polymerization. The lotion that includes microbubbles 240 or microspheres 214 and packing agent 216 can have additional components, such as a carrier, e.g., water or an alcohol, a preservative, or color adhesive dyes that do not wash off.

Monolayer 222 can remain on a user's skin for an extended period of time, e.g., several days, or can be removed and reapplied frequently.

As in the molecular monolayer embodiment, the cosmetic composition of the trapped gas embodiment can also be an aerosolizable liquid for spraying onto skin. The composition can be clear (largely transparent), or color can be added, e.g., by including melanin granules or liganded hemoproteins.

Colored Additives

Human skin includes small, chromophoric structures, such as capillary loops and hair follicles. These structures are typically various shades and tones of black, brown, or red. Since human color vision is capable of perceiving spectral texture which is finer than visual acuity, these chromophoric structures can be "seen" even when they are too small to be individually resolved by the naked eye. In general, the chromophoric structures are more visible and more prominent in older individuals. Cosmetics which cover these small, chromophoric structures with a homogenous coating, therefore, may cause the skin to look unnatural.

To give the skin a more natural appearance, any cosmetic skin lotion, including the anti-reflective cosmetic coatings described above, can be formulated to include colored, shaped additives that mimic the appearance of chromophoric structures in skin. The colored additives are, e.g., fibers, disks, or beads constructed from, e.g., polymers, such as nylon or polyester. The polymers are dyed different colors to mimic the pigments of chromophoric structures, such as small hair follicles, blood vessels, e.g., microvessels or capillary loops, sweat duct openings, freckles, and fine hairs, such as vellus hairs. For example, the polymers can be dyed the color of oxyhemoglobin or melanin. Dyed additives having the desired sizes and shapes can be manufactured using techniques known, e.g., in the textile industry.

Alternatively, the additives can be constructed from natural materials, rather than from polymers. For example, solid particles can be made from melanin found naturally in squid ink.

The additives can be a variety of sizes and shapes, depending on the structures being mimicked. For example, the disc shaped additives can have a diameter, e.g., of about 1 micron. Red Fibers can be the thickness of fine capillaries, e.g., about 10–50 microns, and can be about 20–200 microns long. Brown or black fibers can have the same diameter as vellus hairs, e.g., between 20 and 50 microns. Cosmetics for older individuals might include more additives or coarser additives than cosmetics designed for 50 or 30 year-olds.

The additives can be added to the anti-reflective cosmetic described above, or to other types of cosmetics, such as homogenous, opaque cosmetic lotions and powders having a color similar to the color of skin. The additives can be added to a cosmetic composition either during manufacture of the composition, or by simply mixing them into an existing cosmetic composition.

Other Embodiments

The cosmetic compositions described herein can be varied in a number of respects. For example, the lengths of the molecules forming the molecular monolayer embodiment, or the diameters of the microspheres and microbubbles forming the monolayer of the trapped gas embodiment, can be varied to alter the function of the coating. In one possible application, the thickness of the coating can be controlled to create iridescence. An iridescent coating would differentially reflect light of different wavelengths, depending on the angle of incidence. The iridescent coating, therefore, would appear to have a different color (within a defined wavelength range) depending on the angle from which it is viewed. Similarly, the cosmetic composition can be an iridescent fingernail polish.

Materials that form layers other than molecular monolayers and trapped gas monolayers can be used, so long as the layer formed satisfies the anti-reflective parameters.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An anti-reflective cosmetic composition for skin comprising a material that, when applied to skin, forms a layer of the material that adheres to the skin, has a thickness of from about 60 nm to about 140 nm, and has a refractive index of between about 1.1 and 0.4, wherein the layer of material comprises a trapped gas the form of microbubbles or microspheres having diameters less than about 55 nm to reduce the index of refraction of the layer, and reduces the Fresnel component of light reflected from skin.

2. The cosmetic composition of claim 1, wherein the layer has a thickness of between about 80 nm and 120 nm and a refractive index of between about 1.2 and 1.3.

3. The cosmetic composition of claim 1, wherein the layer is a molecular monolayer.

4. The cosmetic composition of claim 3, wherein the molecular monolayer comprises amphipathic molecules.

5. The cosmetic composition of claim 4, wherein the amphipathic molecules comprise straight-chain phospholipids.

6. The cosmetic composition of claim 4, wherein the amphipathic molecules have lengths of between about 95 nm and 100 nm.

7. The cosmetic composition of claim 4, further comprising a carrier.

8. The cosmetic composition of claim 7, wherein the carrier comprises water.

9. The cosmetic composition of claim 1, wherein the composition comprises an aerosolizable liquid that can be sprayed onto skin to form the layer.

10. The cosmetic composition of claim 1, further comprising a chromophore having a natural skin color.

11. The cosmetic composition of claim 10, wherein the chromophore is selected from the group consisting of melanin granules and liganded hemoproteins.

12. The cosmetic composition of claim 1, wherein the layer is generally translucent.

13. The cosmetic composition of claim 1, wherein the layer is generally transparent.

14. The cosmetic coating of claim 1, wherein the trapped gas is in a microsphere.

15. The cosmetic coating of claim 1, further comprises a packing agent.

16. The cosmetic coating of claim 15, wherein the packing agent comprises a polymer.

17. The cosmetic coating of claim 16, wherein the polymer is selected from the group consisting of polyvinylalcohol polymethyl methacrylate, and polydimethyldiallylammonium.

18. The cosmetic coating of claim 14, wherein the microspheres are encapsulated by a capsule substance comprising a moiety having a negative charge.

19. The cosmetic coating of claim 18, wherein the capsule substance comprises a polycarbonate group.

20. The cosmetic coating of claim 1, wherein the trapped gas is in a microbubble.

21. An anti-reflective cosmetic composition for skin comprising a material that, when applied to skin, forms a layer of the material that adheres to the skin, has a thickness of from about 60 nm to about 140 nm, and has a refractive index of between about 1.1 and 0.4, wherein the layer of material comprises a monomer that when activated polymerizes to form a molecular monolayer, and wherein the monomer includes a moiety having a negative charge, such that the moiety is attracted to stratum corneum.

22. The cosmetic composition of claim 21, wherein the material further comprises a trapped gas to reduce the index of refraction of the layer.

23. The cosmetic composition of claim 22, wherein the trapped gas is in a microsphere.

24. The cosmetic composition of claim 22, wherein the trapped gas is in a microbubble.

25. The cosmetic composition of claim 22, wherein the trapped gas is in the form of microbubbles or microspheres having diameters less than about 55 nm.

26. The cosmetic composition of claim 21, wherein the moiety comprises an amine group or a carboxyl group.

27. The cosmetic composition of claim 21, wherein the activation of the monomer is triggered by application of the material to skin.

28. A method of obscuring wrinkles on skin, the method comprising:

obtaining an anti-reflective cosmetic composition of claim 1; and applying a layer of the anti-reflective cosmetic composition to the skin in an area where wrinkles are to be obscured.

29. The method of claim 28, wherein the layer has a thickness of between about 80 nm and 120 nm and a refractive index of between about 1.2 and 1.3.

30. The method of claim 28, wherein the layer is a molecular monolayer.

31. The method of claim 30, wherein the molecular monolayer comprises amphipathic molecules.

32. The method of claim 31, wherein the amphipathic molecules comprise straight-chain phospholipids.

33. The method of claim 31, wherein the amphipathic molecules have lengths of between about 95 nm and 100 nm.

34. The method of claim 31, wherein the material further comprises a trapped gas to reduce the index of refraction of the layer.

35. The method of claim 30, wherein the material comprises a monomer, wherein the monomer, when activated, polymerizes to form the molecular monolayer.

36. The method of claim 35, wherein the monomer includes a moiety having a negative charge, such that the moiety is attracted to stratum corneum.

37. The method of claim 28, wherein the composition comprises an aerosolizable liquid that can be sprayed onto skin to form the layer.

38. The method of claim 28, wherein the trapped gas is in a microsphere.

* * * * *

UNITED STATES PATENT AND TRADEMARK OFFICE
CERTIFICATE OF CORRECTION

PATENT NO. : 6,491,929 B1
DATED : December 10, 2002
INVENTOR(S) : Richard Rox Anderson

It is certified that error appears in the above-identified patent and that said Letters Patent is hereby corrected as shown below:

Column 9,
Line 44, "0.4" should be -- 1.4 --.
Line 45, after "gas", insert -- in --.

Column 10,
Line 38, "0.4" should be -- 1.4 --.

Signed and Sealed this

Twenty-eighth Day of June, 2005

JON W. DUDAS
*Director of the United States Patent and Trademark Office*